United States Patent [19]
Toy, II

[11] Patent Number: 6,029,901
[45] Date of Patent: Feb. 29, 2000

[54] AIR FRESHENER DISPENSER

[76] Inventor: John S. Toy, II, 19 Saunder St., Allston, Mass. 02134

[21] Appl. No.: 09/195,971

[22] Filed: Nov. 19, 1998

[51] Int. Cl.[7] .................................................. A24F 25/00
[52] U.S. Cl. .............................................. 239/55; 239/59
[58] Field of Search ................................. 239/58, 59, 57, 239/55, 6, 327; 222/215; 428/905

[56] References Cited

U.S. PATENT DOCUMENTS

| | | | |
|---|---|---|---|
| 1,027,856 | 5/1912 | Kocher | 239/59 X |
| 3,770,199 | 11/1973 | Mock | 239/55 X |
| 3,848,803 | 11/1974 | Levey | 239/59 |
| 4,097,637 | 6/1978 | McMillan | 239/58 |
| 4,905,898 | 3/1990 | Wade | 237/58 X |
| 5,064,624 | 11/1991 | King | 239/57 X |
| 5,611,486 | 3/1997 | Paul | 239/58 X |

*Primary Examiner*—Kevin Weldon

[57] ABSTRACT

A air freshener dispenser for dispensing an aroma from a scented liquid to an area. The air freshener dispenser includes a housing with a porous bladder provided therein. The porous bladder is designed for holding a scented liquid therein and has a plurality of pores therethrough designed for permitting the passage therethrough of the aroma of the scented liquid held therein. The porous bladder has a neck portion providing an opening into the porous bladder to permit filling of the porous bladder with a scented liquid. The neck portion of the porous bladder is outwardly extended through a hole through the housing. The housing has a plurality of spaced apart vent slits therethrough to permit passage of the aroma of a scented liquid in the porous bladder to pass out of the housing.

10 Claims, 2 Drawing Sheets

AIR FRESHENER DISPENSER

BACKGROUND OF THE INVENTION

1. Field of the Invention

The present invention relates to air fresheners and more particularly pertains to a new air freshener dispenser for dispensing an aroma from a scented liquid to an area.

2. Description of the Prior Art

The use of air fresheners is known in the prior art. More specifically, air fresheners heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,928,881; U.S. Pat. No. 4,909,438; U.S. Pat. No. 2,802,695; U.S. Pat. No. Des. 374,924; U.S. Pat. No. 5,725,152; and U.S. Pat. No. 2,180,752.

While these devices fulfill their respective, particular objectives and requirements, the aforementioned patents do not disclose a new air freshener dispenser. The inventive device includes a housing with a porous bladder provided therein. The porous bladder is designed for holding a scented liquid therein and has a plurality of pores therethrough designed for permitting the passage therethrough of the aroma of the scented liquid held therein. The porous bladder has a neck portion providing an opening into the porous bladder to permit filling of the porous bladder with a scented liquid. The neck portion of the porous bladder is outwardly extended through a hole through the housing. The housing has a plurality of spaced apart vent slits therethrough to permit passage of the aroma of a scented liquid in the porous bladder to pass out of the housing.

In these respects, the air freshener dispenser according to the present invention substantially departs from the conventional concepts and designs of the prior art, and in so doing provides an apparatus primarily developed for the purpose of dispensing an aroma from a scented liquid to an area.

SUMMARY OF THE INVENTION

In view of the foregoing disadvantages inherent in the known types of air fresheners now present in the prior art, the present invention provides a new air freshener dispenser construction wherein the same can be utilized for dispensing an aroma from a scented liquid to an area.

The general purpose of the present invention, which will be described subsequently in greater detail, is to provide a new air freshener dispenser apparatus and method which has many of the advantages of the air fresheners mentioned heretofore and many novel features that result in a new air freshener dispenser which is not anticipated, rendered obvious, suggested, or even implied by any of the prior art air fresheners, either alone or in any combination thereof.

To attain this, the present invention generally comprises a housing with a porous bladder provided therein. The porous bladder is designed for holding a scented liquid therein and has a plurality of pores therethrough designed for permitting the passage therethrough of the aroma of the scented liquid held therein. The porous bladder has a neck portion providing an opening into the porous bladder to permit filling of the porous bladder with a scented liquid. The neck portion of the porous bladder is outwardly extended through a hole through the housing. The housing has a plurality of spaced apart vent slits therethrough to permit passage of the aroma of a scented liquid in the porous bladder to pass out of the housing.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new air freshener dispenser apparatus and method which has many of the advantages of the air fresheners mentioned heretofore and many novel features that result in a new air freshener dispenser which is not anticipated, rendered obvious, suggested, or even implied by any of the prior art air fresheners, either alone or in any combination thereof.

It is another object of the present invention to provide a new air freshener dispenser which may be easily and efficiently manufactured and marketed.

It is a further object of the present invention to provide a new air freshener dispenser which is of a durable and reliable construction.

An even further object of the present invention is to provide a new air freshener dispenser which is susceptible of a low cost of manufacture with regard to both materials and labor, and which accordingly is then susceptible of low prices of sale to the consuming public, thereby making such air freshener dispenser economically available to the buying public.

Still yet another object of the present invention is to provide a new air freshener dispenser which provides in the apparatuses and methods of the prior art some of the advantages thereof, while simultaneously overcoming some of the disadvantages normally associated therewith.

Still another object of the present invention is to provide a new air freshener dispenser for dispensing an aroma from a scented liquid to an area.

Yet another object of the present invention is to provide a new air freshener dispenser which includes a housing with a porous bladder provided therein. The porous bladder is designed for holding a scented liquid therein and has a plurality of pores therethrough designed for permitting the passage therethrough of the aroma of the scented liquid held therein. The porous bladder has a neck portion providing an opening into the porous bladder to permit filling of the porous bladder with a scented liquid. The neck portion of the porous bladder is outwardly extended through a hole through the housing. The housing has a plurality of spaced apart vent slits therethrough to permit passage of the aroma of a scented liquid in the porous bladder to pass out of the housing.

Still yet another object of the present invention is to provide a new air freshener dispenser that lets a user dispense the aroma from a variety of scented liquids including colognes and perfumes.

Even still another object of the present invention is to provide a new air freshener dispenser that may be used in an area to mask unpleasant odors therein.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
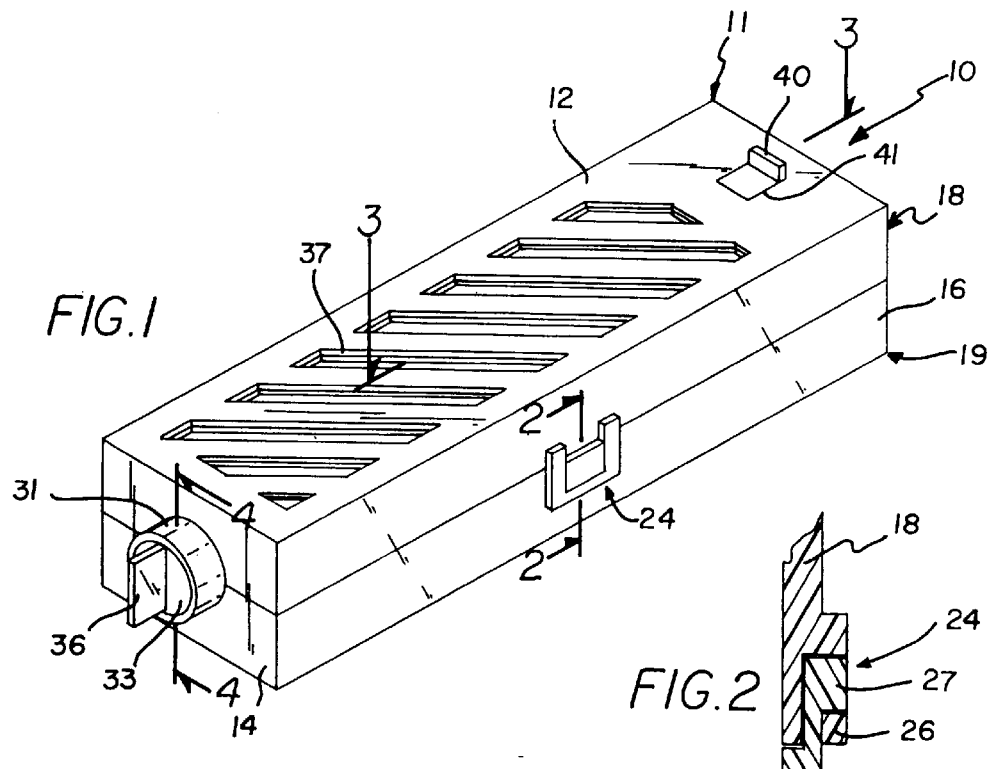
FIG. 1 is a schematic top perspective view of a new air freshener dispenser according to the present invention.
Figure 2:
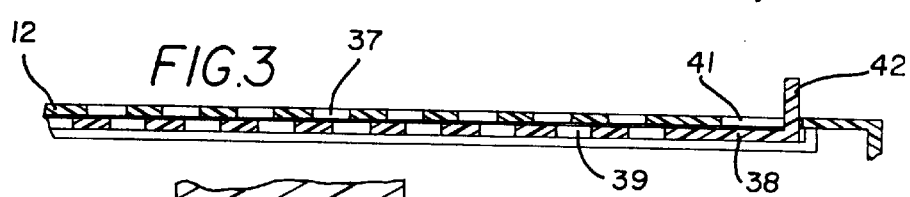
FIG. 2 is a schematic cross sectional view of the present invention taken from line 2—2 of FIG. 1.

With reference now to the drawings, and in particular to FIGS. 1 through 6 thereof, a new air freshener dispenser embodying the principles and concepts of the present invention and generally designated by the reference numeral 10 will be described.

As best illustrated in FIGS. 1 through 6, the air freshener dispenser 10 generally comprises a housing with a porous bladder provided therein. The porous bladder is designed for holding a scented liquid therein and has a plurality of pores therethrough designed for permitting the passage therethrough of the aroma of the scented liquid held therein. The porous bladder has a neck portion providing an opening into the porous bladder to permit filling of the porous bladder with a scented liquid. The neck portion of the porous bladder is outwardly extended through a hole through the housing. The housing has a plurality of spaced apart vent slits therethrough to permit passage of the aroma of a scented liquid in the porous bladder to pass out of the housing.

In closer detail, the air freshener dispenser 10 comprises a housing 11 preferably having spaced apart top and bottom walls 12,13, and a perimeter wall comprising a spaced apart pair of end walls 14,15 and a spaced apart pair of side walls 16,17 extending between the end walls. In one preferred embodiment, the housing is a generally rectangular box shape. Ideally, the corners of the housing are rounded to help prevent injury from abrasive contact with the housing. In another preferred embodiment, the housing is generally cylindrical with the end walls being generally circular.

Figure 5:
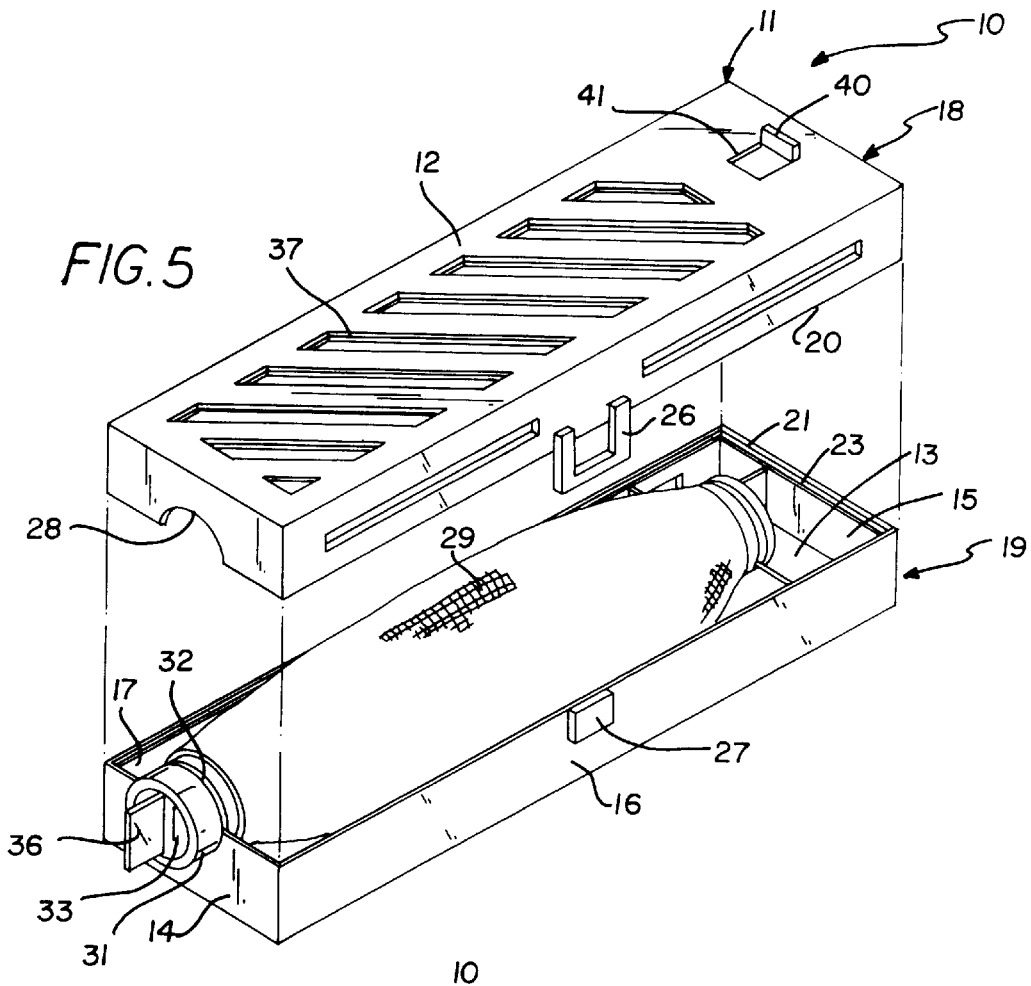
FIG. 5 is a schematic exploded perspective view of the present invention.

As illustrated in FIG. 5, the housing has separable top and bottom portions 18,19. The top portion 18 of the housing includes the top wall 12 and portions of the end walls and side walls of the perimeter wall of the housing. The bottom portion 19 of the housing includes the bottom wall 13 and portions of the end walls and the side walls of the perimeter wall of the housing. The top portion of the housing is coupled to the bottom housing.

The top portion of the housing has a lower edge 20 therearound and the bottom portion of the housing has an upper edge 21 therearound. Preferably, the lower edge of the top portion of the housing has a downwardly depending lower lip 22 therearound while the upper edge of the bottom portion has a shoulder 23 therearound. The lower edge of the top portion of the housing rests on the upper edge of the bottom portion of the housing with the lower lip of the lower edge of the top portion of the housing resting on the shoulder of the upper edge of the bottom portion of the housing.

Preferably, a pair of exterior clip fasteners 24,25 detachably couple the top and bottom portions of the housing together. One of the exterior clip fasteners is located on one of the side walls of the perimeter wall of the housing and the other of the exterior clip fasteners is located on the other side wall of the perimeter wall of the housing. Ideally, each exterior clip fastener comprises a generally rectangular U-shaped clip 26 and a generally rectangular retaining extent 27 which releasably engage one another to couple together the top and bottom portions of the housing. The clips are coupled to the top portion of the housing so that the clips downwardly extend in a direction away from the lower edge of the top portion of the housing. The retaining extents are coupled to the bottom portion of the housing so that the retaining extents upwardly extend from the upper edge of the bottom portion of the housing.

The housing has a generally circular hole 28 therethrough. Preferably, the hole of the housing is located in one of the end walls of the perimeter wall of the housing.

A micro-porous bladder 29 is provided in the housing. The porous bladder is designed for holding a scented liquid therein. The porous bladder has a plurality of micro-pores therethrough designed for permitting the passage therethrough of the aroma of the scented liquid held therein. Preferably, the porous bladder comprises a flexible material to aid the fitting of the porous bladder in the housing, Ideally, the porous bladder comprises micro-porous polytetrafluoroethylene commonly known under the trade name GORE-TEX. In the preferred embodiment, the housing has a plurality of stabilizing ribs 30 therein holding the porous bladder in a position in the housing.

The porous bladder has a generally cylindrical tubular neck portion 31 providing an opening into the porous bladder to permit filling of the porous bladder with a scented liquid. Preferably, the neck portion of the porous bladder comprising a rigid plastic material so that it is relatively non-porous in comparison to the porous bladder. The neck portion of the porous bladder is outwardly extended through the hole of the housing. Preferably, the neck portion of the porous bladder has an annular outer groove 32 therearound. The hole of the housing has a generally circular outer periphery which is extended into the outer groove of the neck portion of the porous bladder to hold the neck portion of the porous bladder in a position in the hole of the housing.

An end cap 33 substantially closes the opening of the neck portion into the porous bladder. Preferably, the lumen of the neck portion has an threaded interior region 34 with an annular gasket therein 35. The end cap is threadably inserted into the threaded interior region of the neck portion to abut the annular gasket. Preferably, the end cap has a finger tab 36 outwardly extended therefrom to aid rotation of the end cap with the fingers of a user to attach and remove the end cap from the neck portion.

Figure 3:
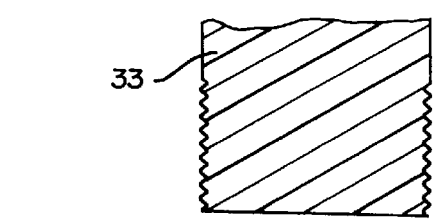
FIG. 3 is a schematic cross sectional view of the present invention taken from line 3—3 of FIG. 1.
Figure 4:
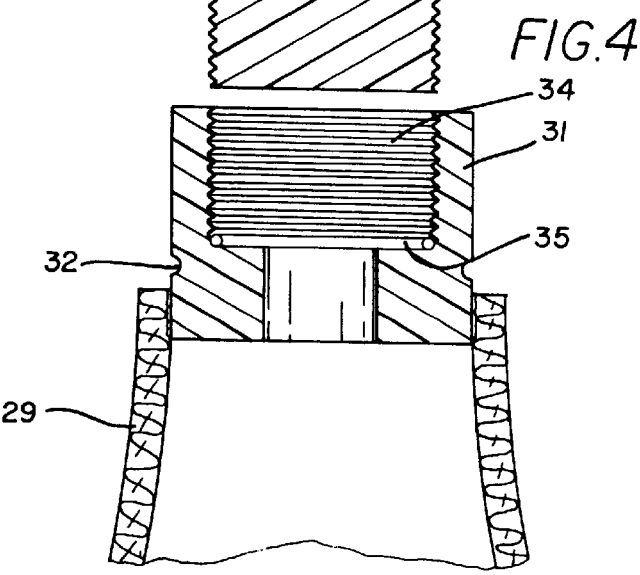
FIG. 4 is a schematic cross sectional view of the present invention taken from line 4—4 of FIG. 1.

With particular reference to FIGS. 1 and 3, the housing has a plurality of spaced apart vent slits 37 therethrough to permit passage of the aroma of a scented liquid in the porous bladder to pass out of the housing. The vent slits of the housing are preferably located on the top panel of the housing. The housing has a longitudinal axis extending between the end walls of the perimeter wall of the housing. Ideally, each of the vent slits of the housing is extended generally parallel to one another and at an acute angle from the longitudinal axis of the housing. As illustrated in FIG. 3, an adjustment panel 38 is slidably mounted in the housing adjacent the slits of the housing to permit sliding of the adjustment panel in directions generally parallel to the longitudinal axis of the housing. The adjustment panel has a plurality of spaced apart adjustment slits 39 therethrough. Each of the adjustment slits of the adjustment is preferably extended generally parallel to one another and at an acute angle to the longitudinal axis of the housing. Preferably, the acute angle of each of the vent slits and the acute angle of each of the adjustment slits are about equal to one another. In use, the adjustment panel is slidable in the housing to a position where the adjustment panel substantially closes the vent slits of the housing to block passage of the aroma of the scented liquid out of the housing through the vent slits. The adjustment panel is also slidable in the housing to permit alignment of each of the adjustment slits with an associated vent slit such that adjustment vents opens passage of aroma out of the housing through the vent slits of the housing.

Preferably, the adjustment panel has a thumb tab 40 outwardly extending through a cutout 41 in the top wall of the housing. In use, the thumb tab is designed for permitting a user to slid the adjustment panel in the housing.

Figure 6:
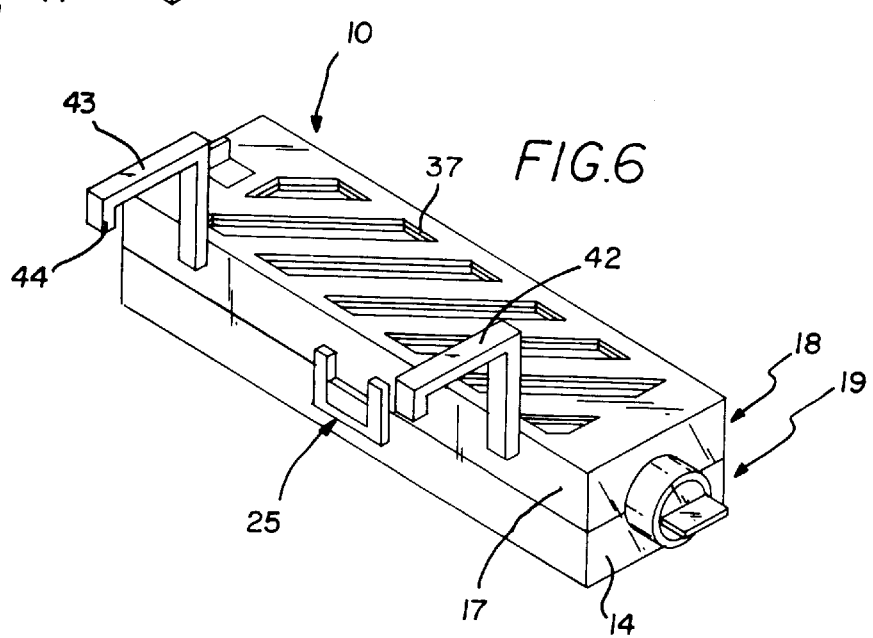
FIG. 6 is a schematic perspective view of an ideal embodiment of the present invention with hanger arms.

In an ideal embodiment illustrated in FIG. 6, the housing has a spaced apart pair of generally inverted-L-shaped hanger arms 42,43 coupled thereto. The hanger arms are preferably positioned on one of the side walls of the perimeter wall of the housing. In use, the hanger arms are designed for hanging on a structure such a rim of a drawer to mount the housing to the structure. Ideally, each of the hanger arms terminates at a hook extent 44 for helping hold the hanger arms on the structure.

The housing has a length defined between the end walls, a width defined between the side walls and a height defined between the top and bottom walls. In an ideal illustrative embodiment, the length of the housing is about 3 inches, the width of the housing is about 1 inch, and the height is between about ½ inch and ¾ inch. This ideal size permits placement of the housing in a variety of small spaces in an area and also is not obtrusive in visibility so that the housing is not easily noticed by others in the area As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An air freshener dispenser, comprising:

a housing;

said housing having a hole therethrough;

a porous bladder being provided in said housing, said porous bladder being adapted for holding a scented liquid therein, said porous bladder having a plurality of pores therethrough adapted for permitting the passage therethrough of the aroma of the scented liquid held therein;

said porous bladder having a neck portion providing an opening into said porous bladder to permit filling of said porous bladder with a scented liquid;

said neck portion of said porous bladder being outwardly extended through said hole of said housing; and said housing having a plurality of spaced apart vent slits therethrough to permit passage of the aroma of a scented liquid in said porous bladder to pass out of said housing.

2. The air freshener dispenser of claim 1, wherein said housing has a spaced apart pair top and bottom walls, and a perimeter wall comprising a spaced apart pair of end walls and a spaced apart pair of side walls extending between said end walls, wherein said hole of said housing is located in one of said end walls of said perimeter wall of said housing, and wherein said vent slits of said housing are located on said top panel of said housing.

3. The air freshening dispenser of claim 1, wherein said housing has separable top and bottom portions, said top portion of said housing having a lower edge, said bottom portion of said housing having an upper edge, said lower edge of said top portion of said housing being coupled to said bottom housing.

4. The air freshening dispenser of claim 3, wherein said lower edge of said top portion of said housing has a downwardly depending lower lip therearound, wherein said upper edge of said bottom portion has a shoulder therearound, wherein said lower edge of said top portion of said housing rests on said upper edge of said bottom portion of said housing, and wherein said lower lip of said lower edge of said top portion of said housing is rested on said shoulder of said upper edge of said bottom portion of said housing.

5. The air freshening dispenser of claim 3, wherein a pair of exterior clip fasteners detachably couple said top and bottom portions of said housing together.

6. The air freshening dispenser of claim 3, wherein each exterior clip fastener comprises a generally rectangular U-shaped clip and a generally rectangular retaining extent, said clip and said retaining extent releasably engaging one another to couple together said top and bottom portions of said housing, said clips being coupled to said top portion of said housing, said clips being downwardly extended in a direction away from said lower edge of said top portion of said housing, said retaining extents being coupled to said bottom portion of said housing, said retaining extents being upwardly extended from said upper edge of said bottom portion of said housing.

7. The air freshener dispenser of claim 1, wherein an end cap substantially closes the opening of said neck portion into said porous bladder.

8. The air freshener dispenser of claim 7, wherein said neck portion has an threaded interior region, said end cap being threadably inserted into said threaded interior region of said neck portion.

9. The air freshener dispenser of claim 1, further comprising an adjustment panel being slidably mounted in said housing adjacent said slits of said housing, said adjustment panel having a plurality of spaced apart adjustment slits therethrough, said adjustment panel being slidable in said housing to a position where said adjustment panel substantially closes said vent slits of said housing, said adjustment panel being slidable in said housing to permit alignment of each of said adjustment slits with an associated vent slit such that adjustment vents opens passage.

10. An air freshener dispenser, comprising:

a housing having a spaced apart pair top and bottom walls, and a perimeter wall comprising a spaced apart pair of end walls and a spaced apart pair of side walls extending between said end walls;

said housing having separable top and bottom portions, said top portion of said housing including said top wall and portions of said end walls and side walls of said perimeter wall of said housing, said bottom portion of said housing including said bottom walls and portions of said end walls and said side walls of said perimeter wall of said housing;

said top portion of said housing having a lower edge, said bottom portion of said housing having an upper edge, said lower edge of said top portion of said housing being coupled to said bottom housing;

said lower edge of said top portion of said housing having a downwardly depending lower lip therearound, said upper edge of said bottom portion having a shoulder therearound;

said lower edge of said top portion of said housing resting on said upper edge of said bottom portion of said housing, said lower lip of said lower edge of said top portion of said housing being rested on said shoulder of said upper edge of said bottom portion of said housing;

wherein a pair of exterior clip fasteners detachably couple said top and bottom portions of said housing together;

one of said exterior clip fasteners being located on one of said side walls of said perimeter wall of said housing, another of said exterior clip fasteners being located on another of said side walls of said perimeter wall of said housing;

each exterior clip fastener comprising a generally rectangular U-shaped clip and a generally rectangular retaining extent, said clip and said retaining extent releasably engaging one another to couple together said top and bottom portions of said housing;

said clips being coupled to said top portion of said housing, said clips being downwardly extended in a direction away from said lower edge of said top portion of said housing, said retaining extents being coupled to said bottom portion of said housing, said retaining extents being upwardly extended from said upper edge of said bottom portion of said housing;

said housing having a generally circular hole therethrough, said hole of said housing being located in one of said end walls of said perimeter wall of said housing;

a porous bladder being provided in said housing, said porous bladder being adapted for holding a scented liquid therein, said porous bladder having a plurality of pores therethrough adapted for permitting the passage therethrough of the aroma of the scented liquid held therein;

wherein said porous bladder comprises a flexible material, wherein said porous bladder comprises micro-porous polytetrafluoroethylene;

said housing having a plurality of stabilizing ribs therein holding said porous bladder in a position in said housing;

said porous bladder having a generally cylindrical tubular neck portion providing an opening into said porous bladder to permit filling of said porous bladder with a scented liquid;

said neck portion of said porous bladder being outwardly extended through said hole of said housing;

said neck portion of said porous bladder having an annular outer groove therearound;

said hole of said housing having an outer periphery, said outer periphery of said hole of said housing being extended into said outer groove of said neck portion of said porous bladder to hold said neck portion of said porous bladder in a position in said hole of said housing;

an end cap substantially closing the opening of said neck portion into said porous bladder, wherein said neck portion has an threaded interior region, said end cap being threadably inserted into said threaded interior region of said neck portion, said end cap having a finger tab being outwardly extended therefrom;

said housing having a plurality of spaced apart vent slits therethrough to permit passage of the aroma of a scented liquid in said porous bladder to pass out of said housing;

said vent slits of said housing being located on said top panel of said housing;

said housing having a longitudinal axis extending between said end walls of said perimeter wall of said housing, each of said vent slits of said housing being extended generally parallel to one another and at an acute angle from said longitudinal axis of said housing;

an adjustment panel being slidably mounted in said housing adjacent said slits of said housing;

said adjustment panel having a plurality of spaced apart adjustment slits therethrough, each of said adjustment slits of said adjustment being extended generally parallel to one another and at an acute angle to said longitudinal axis of said housing;

said acute angle of each of said vent slits and said acute angle of each of said adjustment slits being about equal to one another;

said adjustment panel being slidable in said housing to a position where said adjustment panel substantially closes said vent slits of said housing;

said adjustment panel being slidable in said housing to permit alignment of each of said adjustment slits with an associated vent slit such that adjustment vents opens passage through said vent slits of said housing;

said adjustment panel having a thumb tab outwardly extending through a cutout in said top wall of said housing; and said housing having a spaced apart pair of generally inverted-L-shaped hanger arms coupled thereto, said hanger arms being positioned on one of said side walls of said perimeter wall of said housing, said hanger arms being adapted for hanging on a structure to mount said housing to the structure.

* * * * *